United States Patent [19]

Sayo et al.

[11] Patent Number: 5,502,221

[45] Date of Patent: Mar. 26, 1996

[54] PROCESS FOR PRODUCING CYCLOHEXYLBUTYRIC ACID DERIVATIVE

[75] Inventors: Noboru Sayo; Noboru Sano; Hidenori Kumobayashi, all of Kanagawa, Japan

[73] Assignee: Takasago International Corporation, Tokyo, Japan

[21] Appl. No.: 437,074

[22] Filed: May 5, 1995

Related U.S. Application Data

[60] Division of Ser. No. 175,505, Dec. 30, 1993, Pat. No. 5,442,105, which is a continuation-in-part of Ser. No. 900,444, Jun. 18, 1992, abandoned.

[30] Foreign Application Priority Data

Jun. 21, 1991 [JP] Japan .................... 3-150224

[51] Int. Cl.$^6$ ............................................ C07D 303/38
[52] U.S. Cl. ................................... 549/549; 560/125
[58] Field of Search ...................................... 549/549

[56] References Cited

U.S. PATENT DOCUMENTS

| | | |
|---|---|---|
| 2,446,192 | 1/1946 | Pfister et al. . |
| 4,711,958 | 12/1987 | Iizuka et al. . |
| 4,814,342 | 3/1989 | Hoover et al. . |
| 4,933,482 | 6/1990 | Sayo et al. . |

FOREIGN PATENT DOCUMENTS

| | | |
|---|---|---|
| 0266950 | 5/1988 | European Pat. Off. . |
| 0519763 | 12/1992 | European Pat. Off. . |
| 55-145650 | 11/1980 | Japan . |
| 1-172365 | 7/1989 | Japan . |
| 2-121963 | 5/1990 | Japan . |

OTHER PUBLICATIONS

English–language Abstract of JP–A–2–121963 (May 1990).
English–language Abstract of JP–A–1–172365 (Jul. 1989).
*J. Chem. Soc., Chem. Commun.*, 1989, p. 1678.
*Chem. Lett.*, 1990 p. 723.
*J. Med. Chem.* 1990 33, p. 2707.

*Primary Examiner*—Michael L. Shippen
*Attorney, Agent, or Firm*—Sughrue, Mion, Zinn, Macpeak & Seas

[57] ABSTRACT

A process for for producing a (2R,3S)-cyclohexylnorstatine or a salt thereof is disclosed, which comprises the steps of: enantioselectively hydrogenating a 4-cyclohexyl-2-halogeno-3-oxobutyric acid ester in the presence of a ruthenium-phosphine complex to produce a 4-cyclohexyl-2-halogeno-(3R)-hydroxybutyric acid ester (2); epoxidizing the compound (2) in the presence of a base to produce a 4-cyclohexyl-(2S,3R)-epoxybutyric acid ester (3); reacting the compound (3) with a lower trialkylsilyl azide in the presence of a Lewis acid to produce a (3S)-azide-4-cyclohexyl-(2S)-substituted butyric acid ester (4); subjecting the compound (4) to hydrogenolysis to produce a (2S,3S)-cyclohexylnorstatine derivative (5); and inverting the configuration at the 2-position of the compound (5).

1 Claim, No Drawings

PROCESS FOR PRODUCING CYCLOHEXYLBUTYRIC ACID DERIVATIVE

This is a Divisional of application Ser. No. 08/175,505, filed Dec. 30, 1993, now U.S. Pat. No. 5,492,105, which is a Continuation-in-Part of application Ser. No. 07/900,444, filed Jun. 18, 1992 (abandoned).

FIELD OF THE INVENTION

The present invention relates to a novel process for producing an optically active (2R,3S)-cyclohexylnorstatine represented by formula (9):

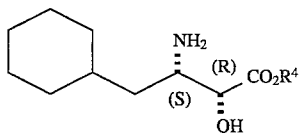

wherein $R^4$ represents hydrogen atom or an alkyl group having from 1 to 7 carbon atoms, which constitutes, specifically as an asymmetric constituent moiety, a peptide compound represented by formula (8):

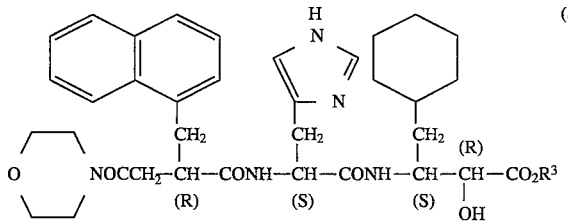

wherein $R^3$ represents an alkyl group having from 1 to 7 carbon atoms, said peptide compound possessing a human renin-inhibiting activity and being useful as a therapeutic agent for hypertension (JP-A-62-234071) (the term "JP-A" as used herein means an "unexamined published Japanese patent application"). The present invention also relates to a cyclohexylbutyric acid derivative useful as an intermediate for the above-described process for producing a norstatine compound.

BACKGROUND OF THE INVENTION

The configuration in the peptide compound represented by the foregoing formula (8) influences the activity. In particular, it has been ascertained that the preferred configuration at the two asymmetric carbon atoms in the carboxylic acid ester moiety is of a (2R,3S)-configuration.

It has, therefore, been desired to develop a process for producing, in an industrially advantageous manner, an optically active (2R,3S)-cyclohexylnorstatine represented by the foregoing formula (9), which constitutes an important asymmetric moiety of the above-described peptide compound.

Hitherto, as a process for producing (2R,3S)-cyclohexylnorstatine, a process in which phenylalanine is used as a raw material is reported in *J. Chem. Soc., Chem. Commun.*, 1989, p. 1678, *Chem. Lett.*, 1990, p. 723, *J. Med. Chem.*, 1990, 33, p. 2707, and JP-A-1-172365. In this process, an alcohol derived from phenylalanine is oxidized to an aldehyde, which has then added thereto prussic acid gas or the like to form two optically active sites. However, this process involves problems in application to commercial production because the process includes the steps of oxidation reaction and of using a toxic cyano compound. In addition, since the aldehyde formed in the course of the process is very unstable, it is likely racemized so that it was extremely difficult to obtain products having a high optical purity.

As another process for producing (2R,3S)-cyclohexylnorstatine, a process for production from a 4-cyclohexylmethyl- 2-azetidinone derivative is reported in JP-A-2-121963. However, this process was also not satisfactory in the yield and optical purity.

In addition, as a process for producing optically active (2S,3S)-cyclohexylnorstatine of formula (10):

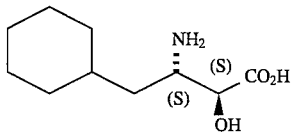

a process for inverting the configuration at the 2-position of the (2R,3S)-isomer is known (*J. Med. Chem.*, 1990, 33, p. 2707).

It is reported in JP-A-63-183551 that Z-4-cyclohexyl-2-buten- 1-ol (3C) is epoxidized to 2(S),3(R)-epoxy-4-cyclohexyl- 1-butanol (3D), which is then oxidized by ruthenium tetrachloride and periodic acid to obtain 2(S),3(R)-epoxy-4-cyclohexyl- 1-butanoic acid (3E').

However, as illustrated in the following reaction scheme, it is considered that compound (3E') described in this Japanese patent is clearly erroneously expressed and should read 2(R),3(R)-epoxy-4-cyclohexyl-1-butanoic acid (3E). This is because while the steric structure at the 2-position is kept by the oxidation of compound (3D), since the carbonyl group is introduced at the 1-position, the steric expression at the 2-position should be (R) but not (S). It is also reported in this Japanese patent that this 2(R),3(R)-epoxy-4-cyclohexyl-1-butanoic acid (3E) is reacted with lithium azide to obtain 3(S)-azido-2(R)-hydroxy-4-cyclohexylbutyric acid (3F).

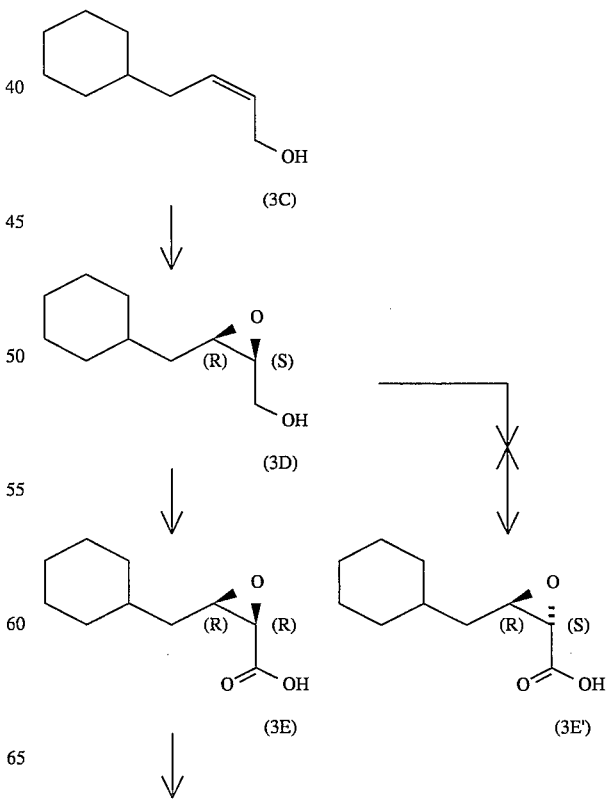

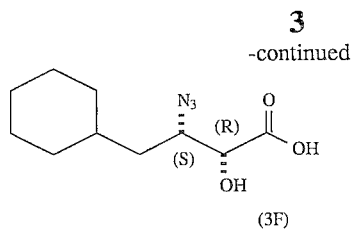

(3F)

SUMMARY OF THE INVENTION

Under these circumstances, the present inventors have conducted extensive and intensive studies. As a result, they have successfully produced an optically active (2R,3S)-cyclohexylnorstatine derivative starting from a 4-cyclohexyl-2-halogeno-3-oxobutyric acid ester, via a novel cyclohexylbutyric acid derivative, leading to accomplishment of the present invention.

Accordingly, an object of the present invention is to provide a process for producing (2R,3S)-cyclohexylnorstatine having a high optical purity in a high yield through simple procedures with safety.

Another object of the present invention is to provide an intermediate useful for production of the above-described norstatine compounds.

Other objects and effects of the present invention will be apparent from the following description.

DETAILED DESCRIPTION OF THE INVENTION

The process of the present invention can be illustrated by the following reaction scheme:

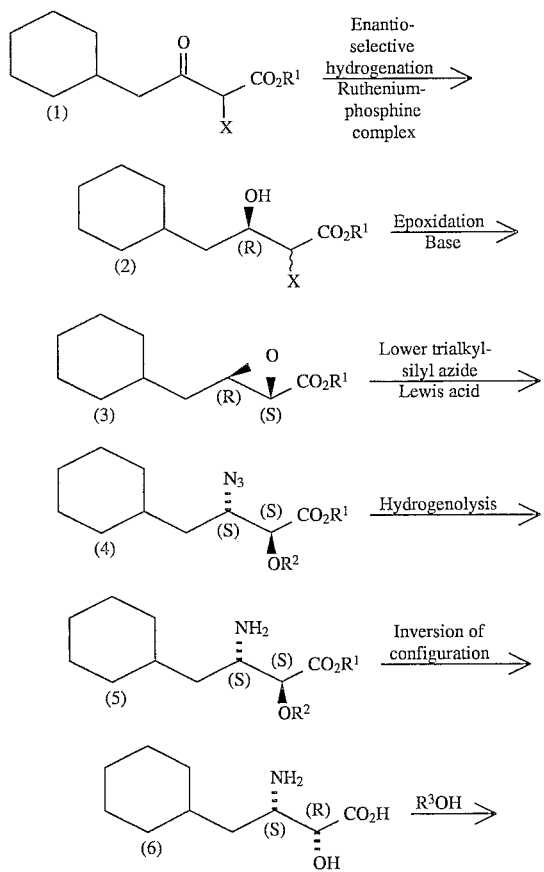

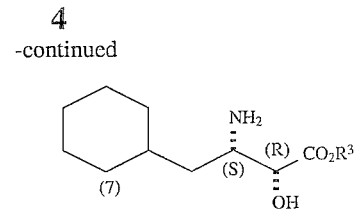

In the above reaction scheme, $R^1$ represents a lower alkyl group; $R^2$ represents a hydrogen atom or a lower trialkylsilyl group; $R^3$ represents an alkyl group having from 1 to 7 carbon atoms; X represents a halogen atom; and the wavy line means a (2S)-configuration and/or a (2R)-configuration.

In one aspect of the present invention, a process is provided, which comprises enantioselectively hydrogenating a 4-cyclohexyl-2-halogeno-3-oxobutyric acid ester (1) in the presence of a ruthenium-phosphine complex to produce a 4-cyclohexyl-2-halogeno-(3R)-hydroxybutyric acid ester (2), epoxidizing the compound (2) in the presence of a base to produce a 4-cyclohexyl-(2S,3R)-epoxybutyric acid ester (3), and then reacting compound (3) with a lower trialkylsilyl azide in the presence of a Lewis acid to produce a (3S)-azido-4-cyclohexyl-(2S)-substituted butyric acid ester (4).

In another aspect of the present invention, a process is provided, which comprises subjecting the (3S)-azido-4-cyclohexyl-(2S)-substituted butyric acid ester (4) to hydrogenolysis to produce a (2S,3S)-cyclohexylnorstatine derivative (5) and then inverting the configuration at the 2-position of the compound (5) to produce (2R,3S)-cyclohexylnorstatine (6) or a salt thereof as described in detail below, and if desired, further reacting the compound (6) or salt thereof with an alcohol [$R^3OH$] to produce a (2R,3S)-cyclohexylnorstatine ester (7).

Examples of the lower alkyl group as referred to herein include alkyl groups having from 1 to 4 carbon atoms. Examples of the lower trialkylsilyl group as also referred to herein include a trimethylsilyl group, a triethylsilyl group, a tripropylsilyl group, a triisopropylsilyl group, a tributylsilyl group, a triisobutylsilyl group, a tert-butyldimethylsilyl group, and a dimethylthexylsilyl.

The starting compound (1) can be obtained by halogenating a 4-cyclohexyl-3-oxobutyric acid ester (*J. Org. Chem.*, 29, 1964, p. 1956).

The 4-cyclohexyl-2-halogeno-(3R)-hydroxybutyric acid ester (2) is obtained by stereoselectively hydrogenating the compound (1) in the presence of a ruthenium-phosphine complex as a catalyst. Examples of the ruthenium-phosphine complex include the ruthnium-phosphine complexes described in JP-A-61-63690 and JP-A-2-191289, and specifically those represented by formulae (11) and (12):

$$Ru_2X_4(R^5\text{-BINAP})_2(NEt_3) \quad (11)$$

In formula (11), $R^5$-BINAP means a tertiary phosphine represented by formula (13):

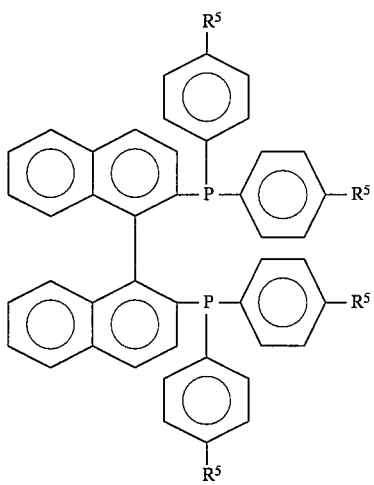

wherein $R^5$ represents a hydrogen atom, a methyl group, a tert-butyl group, or a methoxy group; Et is an ethyl group; and X represents a halogen atom.

$$[RuX(Y)(R^5\text{-BINAP})]X \quad (12)$$

In formula (12), Y represents a phenyl group which may have a substituent group; and Rs-BINAP and X are as defined above.

It is preferred to use the ruthenium-phosphine complex in an amount of from 0.0002 to 0.01 mole, and especially from 0.001 to 0.005 mole per mole of the compound (1). As a solvent for the enantioselective hydrogenation of the compound (1), organic solvents which are ordinarily employed, such as methanol, ethanol, propanol, isopropanol, butanol, tert-butyl alcohol, methylene chloride, tetrahydrofuran, and toluene, can be used. These solvents can also be used in the subsequent reactions. In this enantioselective hydrogenation, it is preferable to use such a solvent in an amount from 2 to 10 times (by volume) the amount of the compound (1).

The reaction for producing the compound (2) is carried out at a temperature of from 0° to 50° C., preferably from 10° to 30° C. under a hydrogen pressure of from 10 to 150 atm., and preferably from 50 to 100 atm. for from 15 to 40 hours. Purification of the thus produced compound (2) can be carried out, for example, by silica gel column chromatography.

The 4-cyclohexyl-(2S,3R)-epoxybutyric acid ester (3) is obtained by reacting the compound (2) with a base at a temperature of from −20° to 30° C., and preferably from −5° to 5° C. for from 1 to 3 hours. Examples of the base include alkali metal alkoxides such as sodium methylate, sodium ethylate, sodium propylate, sodium isopropylate, sodium butylate, sodium tert-butylate, potassium methylate, potassium ethylate, potassium propylate, potassium isopropylate, potassium butylate, and potassium tert-butylate. In this epoxidation of the compound (2), a solvent may be used in an amount from 1 to 3 times (by volume) the amount of the compound (2). Purification of the thus produced compound (3) can be carried out, for example, by adding a phosphoric acid buffer solution (pH 7.0) to the reaction mixture, evaporating off the solvent, extracting the residue with a solvent such as toluene, ethyl acetate, diethyl ether, methylene chloride, and chloroform, evaporating off the solvent, and then subjecting the residue to distillation.

The (3S)-azido-4-cyclohexyl-(2S)-substituted butyric acid ester (4) is obtained by reacting the compound (3) obtained above with a lower trialkylsilyl azide in the presence of a Lewis acid. Thereby to obtain.

Examples of the lower trialkylsilyl azide include trimethylsilyl azide, triethylsilyl azide, tripropylsilyl azide, triisopropylsilyl azide, tributylsilyl azide, triisobutylsilyl azide, tert-butyldimethylsilyl azide, and dimethylthexylsilyl azide.

Examples of the Lewis acid include zinc chloride, zinc bromide, titanium tetrachloride, titanium tetrabromide, aluminum chloride, aluminum bromide, tetraisopropoxytitanium, triisopropoxyaluminum, tin dichloride, and tin tetrachloride. It is preferable to use the lower trialkylsilyl azide in an amount of from 1 to 1.2 mole per mole of the compound (3) and to use the Lewis acid in an amount of from 5 to 20 mol % based on the amount of the compound (3).

The reaction of the compound (3) for producing the compound (4) preferably is conducted at a temperature of from 50° to 100° C., and especially from 60° to 80° C., for from 10 to 30 hours. The thus produced compound (4) can be purified, for example, by silica gel column chromatography.

The optically active (2S,3S)-cyclohexylnorstatine derivative (5) is obtained by hydrogenolysis of the compound (4) in the presence of a catalyst such as a 5 to 10% palladium-on-carbon catalyst in an amount of from 1 to 10% by weight based on the amount of the compound (4). The term "hydrogenolysis" as used herein means a reduction method converting azide into amine by using hydrogen as a reducing agent as follows:

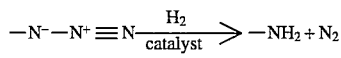

The hydrogenolysis is preferably carried out at a temperature of from 0° to 50° C., and more preferably from 10° to 30° C. under a hydrogen pressure of from 1 to 30 atm., and more preferably from 15 to 25 atm. for from 10 to 40 hours. Although the amount of a solvent used for the hydrogenolysis is not particularly limited, it is desirably from 3 to 5 times (by volume) the amount of the compound (4). In this case, if an alcohol is used as the solvent, the 2-lower trialkylsilyl group is converted to a hydroxyl group. On the other hand, if tetrahydrofuran or the like is used as the solvent, the 2-lower trialkylsilyl group does not change. After the catalyst is removed from the reaction mixture and the solvent is evaporated off, the residue can be purified, for example, by silica gel column chromatography to obtain the compound (5).

Inversion of the configuration of the thus obtained optically active (2S, 3S)-cyclohexylnorstatine derivative (5) to (2R, 3S)-cyclohexylnorstatine (6) can be achieved by a known method (J. Am. Chem. Soc., 1949, vol 71, p. 1101) as illustrated by the following reaction scheme:

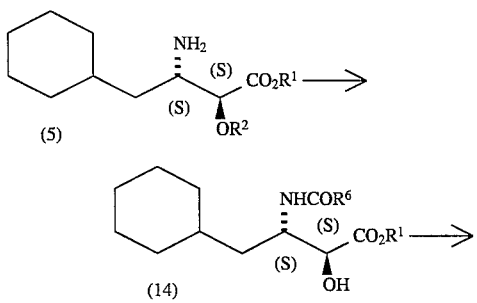

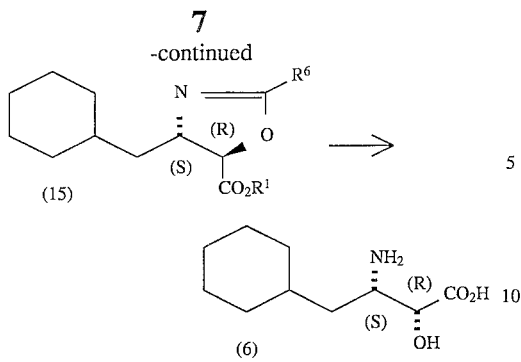

In the above reaction scheme, $R^6$ represents a lower alkyl group or a phenyl group which may have a substituent group; and $R^1$ and $R^2$ are as defined hereinabove.

In the above-illustrated method, the compound (14) is obtained by reacting the compound (5) with an acyl chloride compound in the presence of a base. Examples of the acyl chloride compound include acetyl chloride, propionyl chloride, butyryl chloride, benzoyl chloride, 2-methylbenzoyl chloride, 3-methylbenzoyl chloride, 4-methylbenzoyl chloride, 2-methoxybenzoyl chloride, 3-methoxybenzoyl chloride, 4-methoxybenzoyl chloride, 2-chlorobenzoyl chloride, 3-chlorobenzoyl chloride, 4-chlorobenzoyl chloride, 4-nitrobenzoyl chloride, 3,5-dinitrobenzoyl chloride, and 2,4-dinitrobenzoyl chloride. Examples of the base include trimethylamine, triethylamine, diisopropylethylamine, pyridine, and 4-dimethylaminopyridine. It is preferred to use the base in an amount of from 1 to 1.2 mole per mole of the compound (5).

The reaction of the compound (5) with the acyl chloride compound is conducted at a temperature of from −20° to 30° C. for from 6 to 20 hours. Although the amount of a solvent used is not particularly limited, it is preferably from 3 to 5 times (by volume) the amount of the compound (5). The resulting reaction product can be purified, for example, by silica gel column chromatography after treatment with 1N hydrochloric acid and removal of the solvent by evaporation.

Inversion of the compound (5) to the compound (6) can also be achieved by the following reaction scheme:

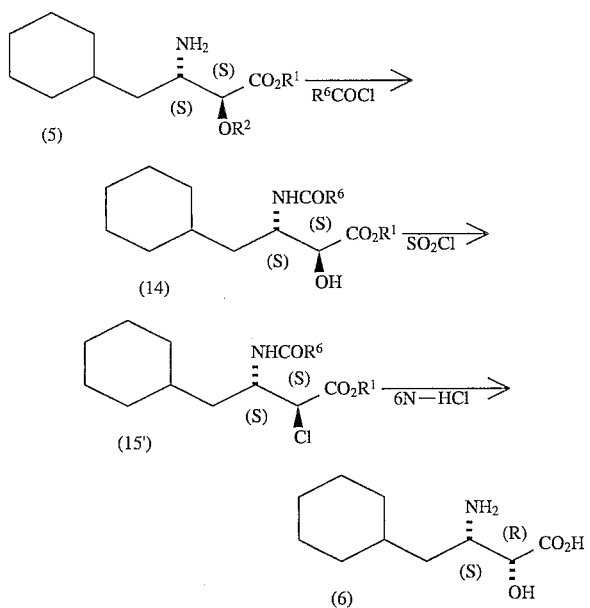

The compound (15') is obtained by reacting the compound (14) with thionyl chloride in an amount of from 1 to 3 moles per mole of the compound (14). This reaction is conducted at a temperature of from −20° to 50° C. for from 1 to 3 hours. Although the amount of a solvent used is not particularly limited, it is preferably from 1 to 3 times (by volume) the amount of the compound (14). After the reaction, the solvent is evaporated off to obtain the compound (15'). In this case, where thionyl chloride is used, the compound (15') is obtained as a hydrochloric acid salt.

The compound (6) is obtained by dissolving the compound (15') in a from 10 to 25% hydrochloric acid in an amount of from 5 to 10 times (by volume) the amount of the compound (15') and allowing the solution to react at a temperature of from 80° to 100° C. for from 5 to 20 hours, followed by concentrating the reaction mixture. In this reaction, where the compound (15') in a hydrochloric acid salt form is used as it is, the compound (6) is obtained also as a hydrochloric acid salt.

The thus obtained compound (6) may be converted to the ester (7). This conversion may be carried out, for example, by dissolving the compound (6) in a mixed solution of dry hydrogen chloride gas and an alcohol, heating the solution at a temperature of from 70° to 100° C. for from 1 to 5 hours to effect esterification, and then neutralizing the reaction product.

Examples of the alcohol for use in the above reaction include methanol, ethanol, propanol, isopropanol, butanol, isobutanol, sec-butyl alcohol, and tert-butyl alcohol. It is preferable to use the mixed solution of dry hydrogen chloride gas and an alcohol in an amount from 3 to 5 times (by volume) the amount of the compound (6).

The neutralization can be achieved by removing the solvent by evaporation, dissolving the residue in a solvent in an amount of from about 3 to 5 times (by volume), adding thereto an aqueous solution of a base in an amount of from about 1 to 3 molar times, and then allowing the mixture to react at a temperature of from −20° to 30° C. Examples of the solvent for use in this neutralization include toluene, tetrahydrofuran, ethyl acetate, chloroform, and methylene chloride. Examples of the base for use in the neutralization include sodium carbonate, sodium hydrogencarbonate, potassium carbonate, and potassium hydrogencarbonate.

After completion of the neutralization operation, the organic layer may be separated from the aqueous layer and then concentrated to obtain the neutralized ester (7). This ester (7) can be purified by recrystallization.

As described above, the process of the present invention is an industrially advantageous process by which an optically active cyclohexylnorstatine having a high optical purity can be produced safely in a good yield.

The present invention will be illustrated in more detail with reference to the following Examples, but the invention is not construed as being limited thereto.

In these Examples, measurements were made using the following analytical instruments and conditions unless otherwise indicated.

1. Gas Chromatography:

Instrument: Shimadzu GC-9A (manufactured by Shimadzu Corporation)

Column: OV-101 Silica Capillary, $\phi$ 0.25 mm× 25 m (manufactured by GL Science Co., Ltd.)

Measuring temperature: heating at a rate of 10° C./min. between 100° and 250° C.

Injection temperature: 200° C.

2. High-Performance Liquid Chromatography (HPLC):

Instrument: Model Waters 510 (manufactured by Waters Inc.)

Detector: UV detector, Model Waters 484 (manufactured by Waters Inc.)

3. NMR:
   Instrument: Model AM-400 (400 MHz) (manufactured by Bruker Inc.)
   Internal standard: tetramethylsilane
4. Optical Rotation Measurement:
   Instrument: Model DIP-4 (manufactured by Nippon Bunko Kogyo K.K.)
5. Elemental Analysis:
   Instrument: Model CHN-2400 (manufactured by Perkin-Elmer Co.)
6. Mass Spectrometry:
   Instrument: Model M80B (manufactured by Hitachi, Ltd.)

EXAMPLE 1

Synthesis of Methyl (2SR)-Chloro-4-cyclohexyl-(3R)-hydroxybutyrate

In a mixed solution of 15 ml of methanol and 105 ml of methylene chloride were dissolved 23.25 g (0.1 mole) of methyl 2-chloro-4-cyclohexyl-3-oxobutyrate and 169 mg (0.1 mmole) of $Ru_2Cl_4((+)-BINAP)_2NEt_3$. The solution was charged into a 500-ml autoclave and reacted under a hydrogen pressure of 100 atm. at 20° C. for 20 hours. The reaction mixture was concentrated and purified by silica gel column chromatography to obtain 23.30 g (percent yield: 99%) of methyl (2SR)-chloro-4-cyclohexyl-(3R)-hydroxybutyrate. Gas chromatographic analysis revealed that the product consisted of 65% of a syn isomer and 35% of an anti isomer.

Optical purity:
  syn isomer 92% ee (96:4)
  anti isomer 82% ee (91:9)

The optical purity of each isomer was determined by reacting 47 mg (0.2 mmole) of methyl (2SR)-chloro-4-cyclohexyl-( 3R)-hydroxybutyrate with 51 mg (0.2 mmole) of (R)-α-methoxy-α-trifluoromethylphenylacetic acid chloride in 1 ml of pyridine for 5 hours to convert the butyrate into an ester of (R)-α-methoxy-α-trifluoromethylphenylacetic acid and then analyzing this ester by HPLC. The following conditions were used for the HPLC analysis.

Column: YMC-PAK A-003-3, φ 4.6 mm×250 mm (manufactured by YMC K.K.)
  Eluent: hexane:tetrahydrofuran=99:1
  Flow rate: 1 ml/min
  Detection wavelength: 254 nm It was also found that the syn isomer had a proportion of the (2S,3R)-isomer to the (2R,3S)-isomer of 96/4, while the anti isomer had a proportion of the (2R,3R)-isomer to the (2S,3S)-isomer of 91/9. This finding was obtained from the data on the compounds synthesized from the above-obtained butyrate in the subsequent Examples.

$^1$H-NMR (CDCl$_3$, δ ppm):
  syn isomer: 0.84 to 1.85 (m, 13H, CH), 2.43 (s, 1H, OH), 3.82 (s, 1H, OH), 3.82 (s, 3H, OCH$_3$), 4.08 to 4.16 (m, 1H, CHO), 4.20 (d, 1H, J=6.50 Hz, CHCl)
  anti isomer: 0.82 to 1.86 (m, 13H, CH), 2.38 (br s, 1H, OH), 3.82 (s, 3H, OCH$_3$), 4.18 to 4.23 (m, 1H, CHO), 4.30 (d, 1H, J=3.98 Hz, CHCl)

EXAMPLE 2

Synthesis of Methyl 4-Cyclohexyl-(2S,3R)-epoxybutyrate

Into a reactor were charged 85 g (0.441 mole) of a 28% sodium methylate solution in methanol and 100 ml of methanol. The mixture was cooled to 5° C. in an ice bath. A solution having 100 g (0.426 mole) of methyl (2SR)-chloro-4-cyclohexyl-( 3R)-hydroxybutyrate as synthesized in Example 1 dissolved in 200 ml of methanol was then added dropwise thereto while ice cooling. After completion of the dropwise addition, the mixture was stirred at 5° C. for 2 hours, and the reaction mixture was then added to 500 ml of a 0.1M phosphoric buffer solution* (pH=7) cooled at 0° C. Subsequently, the methanol was evaporated off under a reduced pressure, the residue was extracted with ethyl acetate, and the solvent was then evaporated off. The residual crude product was purified by simple distillation (102° to 110° C./0.1 mmHg) to obtain 56.91 g (percent yield: 75%) of methyl 4-cyclohexyl-(2S,3R)-epoxybutyrate.

| *:Composition of 0.1M phosphoric buffer solution: | |
|---|---|
| Monosodium phosphate (NaH$_2$PO$_4$.2H$_2$O) | 5.55 g |
| Disodium phosphate (Na$_2$HPO$_4$.12H$_2$O) | 21.5 g |
| Water | 1,000 ml |

GLC analysis revealed that the thus obtained epoxy compound had a a cis/trans ratio of 5/95.

$^1$H-NMR (CDCl$_3$, δ ppm): 0.84 to 1.84 (m, 13H, CH), 3.15 to 3.19 (m, 2H, CH), 3.78 (s, 3H, CH$_3$) [α]$_D$: +30.60° (C=2.25, methanol)

| Elemental analysis for C$_{11}$H$_{18}$O$_3$: | | |
|---|---|---|
| | C | H |
| Calculated (%): | 66.64 | 9.15 |
| Found (%): | 66.39 | 8.91 |

EXAMPLE 3

Synthesis of Methyl (3S)-Azido-4-cyclohexyl-(2S)-trimethylsiloxybutyrate

Into a reactor were charged 14.43 g (72.9 mmole) of methyl 4-cyclohexyl-(2S,3R)-epoxybutyrate as obtained in Example 2, 8.4 g (73 mmole) of trimethylsilyl azide, and 1.0 g (73 mmole) of zinc chloride. The mixture was stirred at 70° C. for 20 hours to allow it to reaction. After completion of the reaction, the reaction product was purified by silica gel column chromatography (hexane:ethyl acetate=9:1 (by volume)) to obtain 20.29 g (percent yield: 91%) of methyl (3S)-azido- 4-cyclohexyl-(2S)-trimethylsiloxybutyrate.

$^1$H-NMR (CDCl$_3$, δ ppm): 0.14 to 0.18 (m, 9H, SiCH$_3$), 0.76 to 1.82 (m, 13H, CH), 3.49 to 3.53 (m, 1H, CHN$_3$), 3.75 (s, 3H, OCH$_3$), 4.34 (d, 1H, J=3.97 Hz, CHO)

| Elemental analysis for C$_{14}$H$_{27}$N$_3$O$_3$Si: | | | |
|---|---|---|---|
| | C | H | N |
| Calculated (%): | 53.64 | 8.68 | 13.40 |
| Found (%): | 53.41 | 8.84 | 13.62 |

EXAMPLE 4

Synthesis of Methyl (3S)-Amino-4-cyclohexyl-(2S)-trimethylsiloxybutyrate

Into a 500-ml autoclave were charged 50.0 g (159.5 mmole) of methyl (3S)-azido-4-cyclohexyl-(2S)-trimethylsiloxybutyrate as obtained in Example 3, 2.5 g (corresponding to 2% by weight of the butyrate) of a 5% palladium-on-carbon catalyst, and 200 ml (corresponding to 4 times (by volume) of the butyrate) of dry tetrahydrofuran, and the mixture was reacted under a hydrogen pressure of 25 atm. at room temperature for 48 hours. After ascertaining by TLC (benzene:ethyl acetate=8:2 (by volume)) that all the raw material had disappeared, the catalyst was removed using a Celite. The solvent was then evaporated off to obtain 36.7 g (percent yield: 80%) of methyl (3S)-amino-4-cyclohexyl-(2S)-trimethylsiloxybutyrate.

| Elemental analysis for $C_{14}H_{29}NO_3Si$: | | | |
|---|---|---|---|
| | C | H | N |
| Calculated (%): | 58.49 | 10.17 | 4.87 |
| Found | 58.72 | 10.52 | 5.18 |

EXAMPLE 5

Synthesis of Methyl (3S)-Benzamino-4-cyclohexyl-(2S)-hydroxybutyrate

Into a reactor were charged 10.0 g (34.8 mmole) of methyl (3S)-amino-4-cyclohexyl-(2S)-trimethylsiloxybutyrate as obtained in Example 4 and 100 ml (corresponding to 10 times (by volume) the butyrate) of dry tetrahydrofuran. The mixture was cooled to 0° C. in an ice bath, and 4.22 g (41.8 mmole) of triethyl amine and then 4.89 g (34.8 mmole) of benzoyl chloride were gradually added thereto dropwise. The temperature was then returned to room temperature, and the mixture was stirred for 16 hours. Subsequently, 10 ml of a 5% hydrochloric acid aqueous solution was added to the reaction mixture to terminate the reaction. The resulting reaction mixture was extracted with ethyl acetate, the solvent was evaporated off, and the residual crude product was then purified by silica gel column chromatography (benzene:ethyl acetate=10:1 to 5:1 (by volume)) to obtain 10.3 g (percent yield: 92%) of methyl (3S)-benzamino- 4-cyclohexyl-(2S)-hydroxybutyrate.

$^1$H-NMR (CDCl$_3$, δ ppm ): 0.78 to 1.94 (m, 13H, CH), 3.82 (s, 3H, OCH$_3$), 4.43 (d, 1H, J=2.95 Hz, CHO), 4.62 to 4.71 (m, 1H, CHN), 6.31 (d, 1H, J=9.06 Hz, NH), 7.40 to 7.80 (m, 5H, ArH)

| Elemental analysis for $C_{18}H_{25}NO_4$: | | | |
|---|---|---|---|
| | C | H | N |
| Calculated (%): | 67.69 | 7.89 | 4.39 |
| Found (%): | 67.38 | 8.23 | 4.66 |

MS m/e: 320(M+1)$^+$

EXAMPLE 6

Synthesis of Methyl (2S)-Chloro-(3S)-Benzamino-4-cyclohexylbutyrate [compound (15'), R$^1$= methyl, R$^6$=phenyl]

6.22 g (19.47 mmole) of methyl (3S)-benzamino-4-cyclohexyl-( 2S)-hydroxybutyrate [compound (14), R$^1$=methyl, R$^6$ =phenyl] was dissolved in 31.1 ml of toluene, 11.68 g (97.37 mmole) of thionyl chloride was added to the solution while ice cooling, and the mixture was then stirred at room temperature for 1 day. After concentrating the solution, the residue was dissolved in 42 ml of diethylether. Then, 1.97 g (2.71 ml) of triethyl amine was added thereto while water washing, and the mixture was stirred for 15 minutes. The salt thus formed was removed, the solvent was evaporated off, and the residual crude product was then purified by silica gel column chromatography (hexane:triethyl amine=10:1) to obtain 6.07 g (percent yield: 92%) of methyl (2S)-chloro-(3S)-benzamino-4-cyclohexylbutyrate.

IR$_{vmax}$, KBr (cm$^{-1}$) 3280, 1745, 1635

$^1$H-NMR (400 MHz, CDCl$_3$, δ ppm): 0.80 to 1.96 (13H, m), 3.84 (3H, s), 4.71 (1H, d, J=4 Hz), 4.82–4.90 (1H, m), 6.59 (1H, d, J=8.9 Hz), 7.40– 7.88 (5H, m)

EXAMPLE 7

Synthesis of (3S)-Amino-4-cyclohexyl-(2R)-hydroxybutyric acid Hydrochloride 3.62 g (10.72 mmol) of methyl (2S)-chloro-(3S)-benzamino- 4-cyclohexylbutyrate [compound (15'), R$^1$=methyl, R$^6$ =phenyl] was added with 72 ml of 6N hydrochloric acid, and the mixture was stirred for 16 hours at 100° C. The reaction mixture was washed with 20 ml of toluene to remove benzoic acid formed, and the resulting aqueous layer was concentrated to obtain 2.41 g (percent yield: 94%) of (3S)-amino-4-cyclohexyl-( 2R)-hydroxybutyric acid hydrochloride.

EXAMPLE 8

Synthesis of Isopropyl (3S)-Amino-4-cyclohexyl(2R)-hydroxybutyrate 4.2 g (14.6 mmole) of (3S)-amino-4-cyclohexyl-(2R)-hydroxybutyric acid hydrochloride as obtained in Example 7 was dissolved in 42 ml (corresponding to 10 times (by volume) of the hydrochloride) of an isopropanol-hydrogen chloride gas solution, and the solution was stirred at 80° C. for 3 hours. After recovering the solvent, the residue was added with chloroform and a saturated sodium hydrogencarbonate aqueous solution. The organic layer was then separated from the aqueous layer and concentrated under a reduced pressure to obtain 4.1 g (percent yield: 95%) of a crude product. This crude product was dissolved in diisopropyl ether, and hexane was added to the solution to recrystallize the reaction product. The thus precipitated white needle crystal was filtered off and dried to obtain 3.36 g (percent yield: 82%) of isopropyl (3S)-amino-4-cyclohexyl-(2R)-hydroxybutyrate. Gas chromatographic analysis revealed that the reaction product thus obtained had a chemical purity of 98%.

m.p.: 85.5° to 86° C.

$[α]_D^{24}$: −21.50° (C=1.03, CHCl$_3$)

$^1$H-NMR (CDCl$_3$, δ ppm): 0.82 to 1.82 (m, 13H, CH), 1.29 (d, J=6.26 Hz, 6H, CH$_3$), 3.20 to 3.90 (m, 1H, CHN), 3.97 (d, J=2.38 Hz, CHO), 5.08 to 5.19 (m, 1H, OCH)

While the invention has been described in detail and with reference to specific embodiments thereof, it will be apparent to one skilled in the art that various changes and modifications can be made therein without departing from the spirit and scope thereof.

What is claimed is:

1. A 4-cyclohexyl-(2S,3R)-epxoybutyric acid ester represented by formula (3):

wherein R$^1$ represents a lower alkyl group.

* * * * *